United States Patent
Murphy et al.

(10) Patent No.: US 9,598,678 B2
(45) Date of Patent: Mar. 21, 2017

(54) MICROBIAL STRAINS AND METHODS OF MAKING AND USING

(71) Applicant: NUtech Ventures, Lincoln, NE (US)

(72) Inventors: Nicole Roswitha Buan Murphy, Lincoln, NE (US); Jennifer Catlett, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 14/689,623

(22) Filed: Apr. 17, 2015

(65) Prior Publication Data

US 2015/0299673 A1 Oct. 22, 2015

Related U.S. Application Data

(60) Provisional application No. 61/980,656, filed on Apr. 17, 2014.

(51) Int. Cl.

| | | |
|---|---|---|
| *C12N 9/02* | (2006.01) | |
| *C12N 1/00* | (2006.01) | |
| *C12N 1/21* | (2006.01) | |
| *C12N 15/00* | (2006.01) | |
| *C12P 5/00* | (2006.01) | |
| *C12P 5/02* | (2006.01) | |
| *C12N 15/52* | (2006.01) | |

(52) U.S. Cl.
CPC ........... *C12N 9/0051* (2013.01); *C12N 15/52* (2013.01); *C12P 5/023* (2013.01); *C12Y 108/98001* (2013.01); *Y02E 50/343* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 2013/0344553 A1* | 12/2013 | Lee ................ C12Y 204/01021 435/160 |

OTHER PUBLICATIONS

Da Graças et al., Genome Announc. e00271-13, 2013, 2 pages.*
UniProt Accession No. Q8TLB2, Apr. 2013, 1 page.*
UniProt Accession No. R7PWB8, Jul. 2013, 1 page.*
Buan and Metcalf, "Methanogenesis by Methanosarcina acetivorans involves two structurally and functionally distinct classes of heterodisulfide reductase," Mol Microbiol. Feb. 2010;75(4):843-53.
Buan et al., "Genetic methods for *methanosarcina* species," Methods Enzymol. 2011;494:23-42.
Chenna et al., "Multiple sequence alignment with the Clustal series of programs," Nucleic Acids Res. Jul. 1, 2003;31(13):3497-500.
Demolli et al., "Development of β-Lactamase as a Tool for Monitoring Conditional Gene Expression by a Tetracycline-Riboswitch in Methanosarcina acetivorans," Archea, 2014, vol. 2014, 10 pages.
Galagan et al., "The genome of M. acetivorans reveals extensive metabolic and physiological diversity," Genome Res. Apr. 2002;12(4):532-42.
GenBank Accession No. AE010299, Mar. 2010, 843 pages.
Thauer et al., "Methanogenic archaea: ecologically relevant differences in energy conservation," Nat Rev Microbiol. Aug. 2008;6(8):579-91.
Thauer, "Biochemistry of methanogenesis: a tribute to Marjory Stephenson. 1998 Marjory Stephenson Prize Lecture," Microbiology. Sep. 1998;144 ( Pt 9):2377-406.
Wolfe, "1776-1996: Alessandro Volta's combustible air," ASM News, 1996 62:529-34.

* cited by examiner

*Primary Examiner* — David J Steadman
(74) *Attorney, Agent, or Firm* — Fish & Richardson P.C.

(57) ABSTRACT

Microbial strains are provided, as are methods of making and using such microbial strains.

15 Claims, 6 Drawing Sheets

SEQUENCE LISTING

<160> NUMBER OF SEQ ID NOS: 22

<210> SEQ ID NO 1
<211> LENGTH: 4101
<212> TYPE: DNA
<213> ORGANISM: Methanosarcina acetivorans

<400> SEQUENCE: 1

```
atgactgacg ggctgaacaa agctgccgta tttatctgcc actgcagcgg gaatatttcc      60
gaacatgttg atattgatgc cgtgaaaaaa acccttaagg cagaagggat ttcggttttt     120
```

```
gattatgagt acatgtgctc aagtcaggga caggctctta ttaaaaagaa gattgtggag    180
gggagcctgg acagggtggt aataggttca tgcactccat ccaaacacgg tactctcttt    240
aaaaagtgca tacaggaaac cggtttgaac agggcagggc ttgaaattgc aaatctcagg    300
gaacaatgtg cctgggtgca ccctgaccgg accggagcta cagaaaaagc tctttccctc    360
ctgagggcca aactcaaacg cctggaaaat gtagagcccc tggatgaaat caaagtcgat    420
atcgctcagc aggcccttgt tatcggtggg ggaatagcag gaattacggc tgcactgaac    480
cttgcagata acggagtttc cactgttctt gttgagaata actcaagcat aggcgggcag    540
atggcaaaaa tcgggaagat attttccccg gacaagcttg ctgaagaatg tgcaatgtgc    600
tctctcagtc ctctgatgaa tgaggttgca gcccacccga aaattacact tttgacccgg    660
accgaagttg aaagcctgag cgggagcgca ggaaacttta cgatcaggct aaggaaaaag    720
ccaagatacg tcaaagacag ctgtacggca tgcgggaggt gcagccgggt ctgtccagtc    780
caggttgaag acgagttcaa ctgcggacat atggacaaaa aggcaatttc tcttcgcttc    840
tcccagtcag tccccaagat ctactgtatt gatcccgatt attgccttca gctgaatggt    900
gaagcctgcg aaaatgtgc ggatgcctgt aaaaacgaag caattgactt ttcccagaag    960
gaagagatcg ttgaacttaa cgtgggggca gttgttgttg ccaccgggtt tgaggagtat   1020
gacgtctccc agaaacccca gtacggatac gggattttcg aaaacgtgct gacccagatg   1080
gaacttgcca gagttcttgg catcaatggc cctacaaaag agaactcct gagagtctca   1140 gatttcagca aagcttccag cgatcctacc cctgcaacct gtgattcaag gtgcgaagat   1200
tcatctgatg aatcccaagg taccgacacg ccaaaaagaa tagtcatgat ccagtgtgtg   1260
ggatcaaggg atgaaaaaga agggggaaac cgctactgtt ccagatactg ctgcatggca   1320
gctctgaaac atgcaagcct gattaagaaa aacatccgg aaacggaaat cacgatttgc    1380
tacattgatg tcagggcttt tggtttctat gaaaattatt accgcgcagt tcaggagacc   1440
ggagtcaact ttgtgcgggg aaggcctgcc gaagttattg aaaagccgga taagagcctt   1500
gttgtaagag tcgaggatac ccttgaccag aaaatgaggg aacttcctgc cgaccttgtt   1560
gtgctttccg cagcaatggt gccttctccc gggaccagga aaattgccag tgtgctgaac   1620
ctgagccagg atgaaagcgg cttttatcaag gaaaggcact ccaagctgaa acccgtggac   1680
agttcccttg acgaatcttt tgtctgcggc actgcccaga gccccaagga cgttaccgat   1740
accattgccc aggcaggact tgcagccgta agggcaaggg cttcattac ggacagcccg    1800 aaggtgctgg ataatgaaat tgcgaccatt aaccagttgc tctgcacgcg ctgcggagaa   1860
tgccttaaat gccccttcga tgccctctcc gtaaatgaga gcggaagggt agtgcttgac   1920
ccgcttatct gcacaggctg cggatactgt accaagctct gcgagaagg agccgtccag   1980 atcgcaggct ttacgaaact ccagctgaaa gccgagatgg agggtgtgct cgaagaaggg   2040
gatgtgctcg gctttgtaaa cagcgggatt gcttcccctta cctgtgacaa tatcggtaac   2100
agtgtgctta cttacccttc gaatgtcaaa ttgataaagg tcccgaccgg ccttgtagtg   2160
gacagagacc tggtgctgca cgccttcagg cacggggcgt cttctgtcct ttttgtagag   2220
gacccaccag acaacccgag ggctgaggtg atatatcctc ttactgtcag ccactttgag   2280
gaactcaaag aggaacttgg agattcagga aaccggatct atttcaaaaa agcatatgtt   2340
ccgaacacaa aagggcttgc aggaactttc accagccttg cccgggaagg agagatgata   2400
agatgatacc atatgtaaag atgatgccat atgtaaacga atacgatacc ccggagtgta   2460
aaactcttgc agagaccgca agaaaaagta tccgaaccccc tgagtccctc ggactggacc   2520
```

```
gctgtatcca gtgcggagcc tgcactgctt cctgtcctgc agcccggttt acggactaca    2580
gcccccgaca gatcgtaaaa aaagtgctcg aaaatgatcg cagtgtgctt gaatccgaaa    2640
tgatctggtc ctgcttctac tgctattcct gcaatttgcg ctgtcccagg aacaacagcc    2700
ccgtaacaat cgtgcaggtt ctccggcaga tggctatcaa cgaaggaatc agggttgaaa    2760
agcttgccta tttccttgag atcggagagc acctcggaga aaacggagcc agcaaggttc    2820
cgggcgctgg catcaaaaac atggaaaaag accttggaga acgctggatt ggaattaaaa    2880
ggaagctgga accaatacgt tccgaacttg gctcagtgc agggatgtc aggaacaccc      2940 atggagaggt tcaggctatt cttgagagca cgggctattt cgaaagggaa aagtggatca    3000
aagcaagggt ccaggaaaag ggaatccggg gttttctgaa gacggaccgc acagggacat    3060
cctgcactga aaagaagaaa aacagcggag acttaggctt tgaaagcgat agagagtata    3120
ccggacagga agctcttact gtttaagagc tgcatggtcg ggcaggaata ccccggaatc    3180
gaaacagcca ccagttacgt gtttgaccgg cttggggtag attactgcat aaacgacgag    3240
cagtcctgct gtacaggaat aggccactat accgatgtct tgaagggct cacaacagcc     3300 gccattgcag cccggaactt tgccgtcgcc agaaagtgcg ggtacccgaa cattacctgc    3360
ctctgttcaa cctgttatgc cataaacaag gacgcatgca aactccttaa caccaacgat    3420
ggggtccggg aaaagtcaa ctccatcttc cgggaaaaag ctttgatga ccttgtctat      3480 gaaaaggact ccatgaaccc cagaaccaat atctatcacg cagtcgaggt cctcctgagc    3540
aaagtcgaaa gatccgggga agagataaag ttcgatttcc ccggcgttaa agcagcctct    3600
catcacgcct gccactatta taaagtcaaa taccttgacg taatcggaaa ccccgaaaac    3660
ccccagctta tagacacgat agccgaagcc tgcggggcat ccctgtgcg ctggtacgaa     3720 gatcgaaccc tcacctgcgg aatgggcttt tcccagctcc acctcaataa aagcacctct    3780
ctccaggtta ccaaaacaaa acttgacagc ctccagagag ccggtgtgga gctaatgatc    3840
catatgtgcc cgaactgcca tatccagtac gaccgctacc agcccgttat cgaaaaagag    3900
ttcggggttg agtacgacat ggtgcacatg aacattgccc agttcgtagc cctctcaatg    3960
ggagcagacc cctacaaagt atgcggtttc cagactcact ccgtgcctct ggaaggattt    4020
cttgaaaaga ccggaataat ataatgtcca gtttcaaagt agaactggct acctttttta    4080
ttacatcggg agtgaagagg g                                              4101

<210> SEQ ID NO 2
<211> LENGTH: 801
<212> TYPE: PRT
<213> ORGANISM: Methanosarcina acetivorans

<400> SEQUENCE: 2

Met Thr Asp Gly Leu Asn Lys Ala Ala Val Phe Ile Cys His Cys Ser
  1               5                  10                  15

Gly Asn Ile Ser Glu His Val Asp Ile Asp Ala Val Lys Lys Thr Leu
             20                  25                  30

Lys Ala Glu Gly Ile Ser Val Phe Asp Tyr Glu Tyr Met Cys Ser Ser
         35                  40                  45

Gln Gly Gln Ala Leu Ile Lys Lys Ile Val Glu Gly Ser Leu Asp
     50                  55                  60

Arg Val Val Ile Gly Ser Cys Thr Pro Ser Lys His Gly Thr Leu Phe
 65                  70                  75                  80

Lys Lys Cys Ile Gln Glu Thr Gly Leu Asn Arg Ala Gly Leu Glu Ile
                 85                  90                  95
```

```
Ala Asn Leu Arg Glu Gln Cys Ala Trp Val His Pro Asp Arg Thr Gly
                100                 105                 110
Ala Thr Glu Lys Ala Leu Ser Leu Leu Arg Ala Lys Leu Lys Arg Leu
            115                 120                 125
Glu Asn Val Glu Pro Leu Asp Glu Ile Lys Val Asp Ile Ala Gln Gln
        130                 135                 140
Ala Leu Val Ile Gly Gly Ile Ala Gly Ile Thr Ala Ala Leu Asn
145                 150                 155                 160
Leu Ala Asp Asn Gly Val Ser Thr Val Leu Val Glu Asn Asn Ser Ser
                165                 170                 175
Ile Gly Gly Gln Met Ala Lys Ile Gly Lys Ile Phe Ser Pro Asp Lys
            180                 185                 190
Leu Ala Glu Glu Cys Ala Met Cys Ser Leu Ser Pro Leu Met Asn Glu
        195                 200                 205
Val Ala Ala His Pro Lys Ile Thr Leu Leu Thr Arg Thr Glu Val Glu
210                 215                 220
Ser Leu Ser Gly Ser Ala Gly Asn Phe Thr Ile Arg Leu Arg Lys Lys
225                 230                 235                 240
Pro Arg Tyr Val Lys Asp Ser Cys Thr Ala Cys Gly Arg Cys Ser Arg
                245                 250                 255
Val Cys Pro Val Gln Val Glu Asp Glu Phe Asn Cys Gly His Met Asp
            260                 265                 270
Lys Lys Ala Ile Ser Leu Arg Phe Ser Gln Ser Val Pro Lys Ile Tyr
        275                 280                 285
Cys Ile Asp Pro Asp Tyr Cys Leu Gln Leu Asn Gly Glu Ala Cys Gly
        290                 295                 300
Lys Cys Ala Asp Ala Cys Lys Asn Glu Ala Ile Asp Phe Ser Gln Lys
305                 310                 315                 320
Glu Glu Ile Val Glu Leu Asn Val Gly Ala Val Val Ala Thr Gly
                325                 330                 335
Phe Glu Glu Tyr Asp Val Ser Gln Lys Pro Gln Tyr Gly Tyr Gly Ile
            340                 345                 350
Phe Glu Asn Val Leu Thr Gln Met Glu Leu Ala Arg Val Leu Gly Ile
        355                 360                 365
Asn Gly Pro Thr Lys Gly Glu Leu Leu Arg Val Ser Asp Phe Ser Lys
        370                 375                 380
Ala Ser Ser Asp Pro Thr Pro Ala Thr Cys Asp Ser Arg Cys Glu Asp
385                 390                 395                 400
Ser Ser Asp Glu Ser Gln Gly Thr Asp Thr Pro Lys Arg Ile Val Met
                405                 410                 415
Ile Gln Cys Val Gly Ser Arg Asp Glu Lys Glu Gly Asn Arg Tyr
            420                 425                 430
Cys Ser Arg Tyr Cys Cys Met Ala Ala Leu Lys His Ala Ser Leu Ile
        435                 440                 445
Lys Lys Lys His Pro Glu Thr Glu Ile Thr Ile Cys Tyr Ile Asp Val
        450                 455                 460
Arg Ala Phe Gly Phe Tyr Glu Asn Tyr Arg Ala Val Gln Glu Thr
465                 470                 475                 480
Gly Val Asn Phe Val Arg Gly Arg Pro Ala Glu Val Ile Glu Lys Pro
                485                 490                 495
Asp Lys Ser Leu Val Val Arg Val Glu Asp Thr Leu Asp Gln Lys Met
            500                 505                 510
```

```
Arg Glu Leu Pro Ala Asp Leu Val Leu Ser Ala Ala Met Val Pro
            515                 520                 525

Ser Pro Gly Thr Arg Lys Ile Ala Ser Val Leu Asn Leu Ser Gln Asp
530                 535                 540

Glu Ser Gly Phe Ile Lys Glu Arg His Ser Lys Leu Lys Pro Val Asp
545                 550                 555                 560

Ser Ser Leu Asp Gly Ile Phe Val Cys Gly Thr Ala Gln Ser Pro Lys
                565                 570                 575

Asp Val Thr Asp Thr Ile Ala Gln Ala Gly Leu Ala Ala Val Arg Ala
            580                 585                 590

Arg Ala Phe Ile Thr Asp Ser Pro Lys Val Leu Asp Asn Glu Ile Ala
            595                 600                 605

Thr Ile Asn Gln Leu Leu Cys Thr Arg Cys Gly Glu Cys Leu Lys Cys
            610                 615                 620

Pro Phe Asp Ala Leu Ser Val Asn Glu Ser Gly Arg Val Val Leu Asp
625                 630                 635                 640

Pro Leu Ile Cys Thr Gly Cys Gly Tyr Cys Thr Lys Leu Cys Gly Glu
                645                 650                 655

Gly Ala Val Gln Ile Ala Gly Phe Thr Lys Leu Gln Leu Lys Ala Glu
            660                 665                 670

Met Glu Gly Val Leu Glu Gly Asp Val Leu Gly Phe Val Asn Ser
            675                 680                 685

Gly Ile Ala Ser Leu Thr Cys Asp Asn Ile Gly Asn Ser Val Leu Thr
            690                 695                 700

Tyr Pro Ser Asn Val Lys Leu Ile Lys Val Pro Thr Gly Leu Val Val
705                 710                 715                 720

Asp Arg Asp Leu Val Leu His Ala Phe Arg His Gly Ala Ser Ser Val
                725                 730                 735

Leu Phe Val Glu Asp Pro Pro Asp Asn Pro Arg Ala Glu Val Ile Tyr
            740                 745                 750

Pro Leu Thr Val Ser His Phe Glu Glu Leu Lys Glu Glu Leu Gly Asp
            755                 760                 765

Ser Gly Asn Arg Ile Tyr Phe Lys Lys Ala Tyr Val Pro Asn Thr Lys
770                 775                 780

Gly Leu Ala Gly Thr Phe Thr Ser Leu Ala Arg Glu Gly Glu Met Ile
785                 790                 795                 800

Arg

<210> SEQ ID NO 3
<211> LENGTH: 314
<212> TYPE: PRT
<213> ORGANISM: Methanosarcina acetivorans

<400> SEQUENCE: 3

Leu Lys Ala Ile Glu Ser Ile Pro Asp Arg Lys Leu Leu Phe Lys
1               5                   10                  15

Ser Cys Met Val Gly Gln Glu Tyr Pro Gly Ile Glu Thr Ala Thr Ser
                20                  25                  30

Tyr Val Phe Asp Arg Leu Gly Val Asp Tyr Cys Ile Asn Asp Glu Gln
            35                  40                  45

Ser Cys Cys Thr Gly Ile Gly His Tyr Thr Asp Val Phe Glu Gly Leu
        50                  55                  60

Thr Thr Ala Ala Ile Ala Ala Arg Asn Phe Ala Val Ala Arg Lys Cys
65                  70                  75                  80
```

Gly Tyr Pro Asn Ile Thr Cys Leu Cys Ser Thr Cys Tyr Ala Ile Asn
                85                  90                  95

Lys Asp Ala Cys Glu Leu Leu Asn Thr Asn Asp Gly Val Arg Glu Lys
            100                 105                 110

Val Asn Ser Ile Phe Arg Glu Lys Gly Phe Asp Asp Leu Val Tyr Glu
        115                 120                 125

Lys Asp Ser Met Asn Pro Arg Thr Asn Ile Tyr His Ala Val Glu Val
    130                 135                 140

Leu Leu Ser Lys Val Glu Lys Ile Arg Glu Glu Ile Lys Phe Asp Phe
145                 150                 155                 160

Pro Gly Val Lys Ala Ala Ser His His Ala Cys His Tyr Tyr Lys Val
                165                 170                 175

Lys Tyr Leu Asp Val Ile Gly Asn Pro Glu Asn Pro Gln Leu Ile Asp
            180                 185                 190

Thr Ile Ala Glu Ala Cys Gly Ala Ser Pro Val Arg Trp Tyr Glu Asp
        195                 200                 205

Arg Thr Leu Thr Cys Gly Met Gly Phe Ser Gln Leu His Leu Asn Lys
    210                 215                 220

Ser Thr Ser Leu Gln Val Thr Lys Thr Lys Leu Asp Ser Leu Gln Arg
225                 230                 235                 240

Ala Gly Val Glu Leu Met Ile His Met Cys Pro Asn Cys His Ile Gln
                245                 250                 255

Tyr Asp Arg Tyr Gln Pro Val Ile Glu Lys Glu Phe Gly Val Glu Tyr
            260                 265                 270

Asp Met Val His Met Asn Ile Ala Gln Phe Val Ala Leu Ser Met Gly
        275                 280                 285

Ala Asp Pro Tyr Lys Val Cys Gly Phe Gln Thr His Ser Val Pro Leu
    290                 295                 300

Glu Gly Phe Leu Glu Lys Thr Gly Ile Ile
305                 310

<210> SEQ ID NO 4
<211> LENGTH: 247
<212> TYPE: PRT
<213> ORGANISM: Methanosarcina acetivorans

<400> SEQUENCE: 4

Met Ile Pro Tyr Val Lys Met Met Pro Tyr Val Asn Glu Tyr Asp Thr
1               5                   10                  15

Pro Glu Cys Lys Thr Leu Ala Glu Thr Ala Lys Lys Ser Ile Arg Thr
            20                  25                  30

Pro Glu Ser Leu Gly Leu Asp Arg Cys Ile Gln Cys Gly Ala Cys Thr
        35                  40                  45

Ala Ser Cys Pro Ala Ala Arg Phe Thr Asp Tyr Ser Pro Arg Gln Ile
    50                  55                  60

Val Lys Lys Val Leu Glu Asn Asp Arg Ser Val Leu Glu Ser Glu Met
65                  70                  75                  80

Ile Trp Ser Cys Phe Tyr Cys Tyr Ser Cys Asn Leu Arg Cys Pro Arg
                85                  90                  95

Asn Asn Ser Pro Val Thr Ile Val Gln Val Leu Arg Gln Met Ala Ile
            100                 105                 110

Asn Glu Gly Ile Arg Val Glu Lys Leu Ala Tyr Phe Leu Glu Ile Gly
        115                 120                 125

Glu His Leu Gly Glu Asn Gly Ala Ser Lys Val Pro Gly Ala Gly Ile
    130                 135                 140

```
Lys Asn Met Glu Lys Asp Leu Gly Glu Arg Trp Ile Gly Ile Lys Arg
145                 150                 155                 160

Lys Leu Glu Pro Ile Arg Ser Glu Leu Gly Leu Ser Ala Arg Asp Val
                165                 170                 175

Arg Asn Thr His Gly Glu Val Gln Ala Ile Leu Glu Ser Thr Gly Tyr
            180                 185                 190

Phe Glu Arg Glu Lys Trp Ile Lys Ala Arg Val Gln Glu Lys Gly Ile
        195                 200                 205

Arg Gly Phe Leu Lys Thr Asp Arg Thr Gly Thr Ser Cys Thr Glu Lys
    210                 215                 220

Lys Lys Asn Ser Gly Asp Leu Gly Phe Glu Ser Asp Arg Glu Tyr Thr
225                 230                 235                 240

Gly Gln Glu Ala Leu Thr Val
                245

<210> SEQ ID NO 5
<211> LENGTH: 4101
<212> TYPE: DNA
<213> ORGANISM: Methanosarcina acetivorans
<220> FEATURE:
<223> OTHER INFORMATION: mutant

<400> SEQUENCE: 5
```

| | | | | |
|---|---|---|---|---|
| atgactgacg | ggctgaacaa | agctgccgta | tttatctgcc | actgcagcgg | gaatatttcc | 60 |
| gaacatgttg | atattgatgc | cgtgaaaaaa | acccttaagg | cagaagggat | ttcggttttt | 120 |
| gattatgagt | acatgtgctc | aagtcaggga | caggctctta | ttaaaaagaa | gattgtggag | 180 |
| gggagcctgg | acagggtggt | aataggttca | tgcactccat | ccaaacacgg | tactctcttt | 240 |
| aaaaagtgca | tacaggaaac | cggtttgaac | agggcagggc | ttgaaattgc | aaatctcagg | 300 |
| gaacaatgtg | cctgggtgca | ccctgaccgg | accggagcta | cagaaaaagc | tctttccctc | 360 |
| ctgagggcca | aactcaaacg | cctggaaaat | gtagagcccc | tggatgaaat | caaagtcgat | 420 |
| atcgctcagc | aggcccttgt | tatcggtggg | ggaatagcag | gaattacggc | tgcactgaac | 480 |
| cttgcagata | acggagtttc | cactgttctt | gttgagaata | actcaagcat | aggcgggcag | 540 |
| atggcaaaaa | tcgggaagat | attttccccg | gacaagcttg | ctgaagaatg | tgcaatgtgc | 600 |
| tctctcagtc | ctctgatgaa | tgaggttgca | gcccacccga | aaattacact | tttgacccgg | 660 |
| accgaagttg | aaagcctgag | cgggagcgca | ggaaacttta | cgatcaggct | aaggaaaaag | 720 |
| ccaagatacg | tcaaagacag | ctgtacggca | tgcgggaggt | gcagccgggt | ctgtccagtc | 780 |
| caggttgaag | acgagttcaa | ctgcggacac | atggacaaaa | aggcaatttc | tcttcgcttc | 840 |
| tcccagtcag | tccccaagat | ctactgtatt | gatcccgatt | attgccttca | gctgaatggt | 900 |
| gaagcctgcg | gaaatgtgc | ggatgcctgt | aaaaacgaag | caattgactt | tcccagaag | 960 |
| gaagagatcg | ttgaacttaa | cgtgggggca | gttgttgttg | ccaccgggtt | tgaggagtat | 1020 |
| gacgtctccc | agaaaccccca | gtacggatac | gggattttcg | aaaacgtgct | gacccagatg | 1080 |
| gaacttgcca | gagttcttgg | catcaatggc | cctacaaaag | agaactcct | gagagtctca | 1140 |
| gatttcagca | agcttccag | cgatcctacc | cctgcaacct | gtgattcaag | gtgcgaagat | 1200 |
| tcatctgatg | aatcccaagg | taccgacacg | ccaaaaagaa | tagtcatgat | ccagtgtgtg | 1260 |
| ggatcaaggg | atgaaaaaga | aggggggaaac | cgctactgtt | ccagatactg | ctgcatggca | 1320 |
| gctctgaaac | atgcaagcct | gattaagaaa | aacatccgg | aaacggaaat | cacgatttgc | 1380 |
| tacattgatg | tcagggcttt | tggtttctat | gaaaattatt | accgcgcagt | tcaggagacc | 1440 |

```
ggagtcaact tgtgcgggg aaggcctgcc gaagttattg aaaagccgga taagagcctt    1500
gttgtaagag tcgaggatac ccttgaccag aaaatgaggg aacttcctgc cgaccttgtt    1560
gtgctttccg cagcaatggt gccttctccc gggaccagga aaattgccag tgtgctgaac    1620
ctgagccagg atgaaagcgg ctttatcaag gaaaggcact ccaagctgaa acccgtggac    1680
agttcccttg acggaatctt tgtctgcggc actgcccaga gccccaagga cgttaccgat    1740
accattgccc aggcaggact tgcagccgta agggcaaggg cttccattac ggacagcccg    1800
aaggtgctgg ataatgaaat tgcgaccatt aaccagttgc tctgcacgcg ctgcggagaa    1860
tgccttaaat gccccttcga tgccctctcc gtaaatgaga gcggaagggg agtgcttgac    1920
ccgcttatct gcacaggctg cggatactgt accaagctct gcggagaagg agccgtccag    1980
atcgcaggct ttacgaaact ccagctgaaa gccgagatgg agggtgtgct cgaagaaggg    2040
gatgtgctcg gctttgtaaa cagcgggatt gcttcccttta cctgtgacaa tatcggtaac    2100
agtgtgctta cttacccttc gaatgtcaaa ttgataaagg tcccgaccgg ccttgtagtg    2160
gacagagacc tggtgctgca cgccttcagg cacgggcgt cttctgtcct ttttgtagag    2220
gaccccaccag acaacccgag ggctgaggtg atatatcctc ttactgtcag ccactttgag    2280
gaactcaaag aggaacttgg agattcagga aaccggatct atttcaaaaa agcatacgtt    2340
ccgaacacaa aagggcttgc aggaactttc accagccttg cccgggaagg agagatgata    2400
agatgatacc ctatgtaaag atgatgccct atgtaaacga atacgatacc ccggagtgta    2460
aaactcttgc agagaccgca aagaaaagta tccgaacccc tgagtccctc ggactggacc    2520
gctgtatcca gtgcggagcc tgcactgctt cctgtcctgc agcccggttt acggactaca    2580
gcccccgaca gatcgtaaaa aaagtgctcg aaaatgatcg cagtgtgctt gaatccgaaa    2640
tgatctggtc ctgcttctac tgctattcct gcaatttgcg ctgtcccagg aacaacagcc    2700
ccgtaacaat cgtgcaggtt ctccggcaga tggctatcaa cgaaggaatc agggttgaaa    2760
agcttgccta tttccttgag atcggagagc acctcggaga aaacggagcc agcaaggttc    2820
cgggcgctgg catcaaaaac atggaaaaag accttggaga acgctggatt ggaattaaaa    2880
ggaagctgga accaatacgt tccgaacttg ggctcagtgc cagggatgtc aggaacaccc    2940
atggagaggt tcaggctatt cttgagagca cgggctattt cgaaagggaa aagtggatca    3000
aagcaagggt ccaggaaaag ggaatccggg gttttctgaa gacggaccgc acagggacat    3060
cctgcactga aaagaagaaa aacagcggag acttaggctt tgaaagcgat agagagtata    3120
ccggacagga agctcttact gtttaagagc tgcatggtcg ggcaggaata ccccggaatc    3180
gaaacagcca ccagttacgt gtttgaccgg cttggggtag attactgcat aaacgacgag    3240
cagtcctgct gtacaggaat aggccactat accgatgtct ttgaagggct cacaacagcc    3300
gccattgcag cccggaactt tgccgtcgcc agaaagtgcg ggtacccgaa cattacctgc    3360
ctctgttcaa cctgttatgc cataaacaag gacgcatgcg aactccttaa caccaacgat    3420
ggggtccggg aaaaagtcaa ctccatcttc cgggaaaaag ctttgatga ccttgtctat    3480
gaaaaggact ccatgaaccc cagaaccaat atctatcacg cagtcgaggt cctcctgagc    3540
aaagtcgaaa agatccggga agagataaag ttcgatttcc ccggcgttaa agcagcctct    3600
catcacgcct gccactatta taaagtcaaa taccttgacg taatcggaaa ccccgaaaac    3660
ccccagctta tagacacgat agccgaagcc tgcggggcat cccctgtgcg ctggtacgaa    3720
gatcgaaccc tcacctgcgg aatgggcttt tcccagctcc acctcaataa aagcacctct    3780
ctccaggtta ccaaaacaaa acttgacagc ctccagagag ccggtgtgga gctaatgatc    3840
```

```
catgtgtgcc cgaactgcca tatccagtac gaccgctacc agcccgttat cgaaaaagag   3900
ttcggggttg agtacgacat ggtgcacatg aacattgccc agttcgtagc cctctcaatg   3960
ggagcagacc cctacaaagt atgcggtttc cagactcact ccgtgcctct ggaaggattt   4020
cttgaaaaga ccggaataat ataatgtcca gtttcaaagt agaactggct accttttta    4080 ttacatcggg agtgaagagg g                                             4101
```

<210> SEQ ID NO 6
<211> LENGTH: 314
<212> TYPE: PRT
<213> ORGANISM: Methanosarcina acetivorans
<220> FEATURE:
<223> OTHER INFORMATION: mutant

<400> SEQUENCE: 6

```
Leu Lys Ala Ile Glu Ser Ile Pro Asp Arg Lys Leu Leu Leu Phe Lys
  1               5                  10                  15

Ser Cys Met Val Gly Gln Glu Tyr Pro Gly Ile Glu Thr Ala Thr Ser
             20                  25                  30

Tyr Val Phe Asp Arg Leu Gly Val Asp Tyr Cys Ile Asn Asp Glu Gln
         35                  40                  45

Ser Cys Cys Thr Gly Ile Gly His Tyr Thr Asp Val Phe Glu Gly Leu
     50                  55                  60

Thr Thr Ala Ala Ile Ala Ala Arg Asn Phe Ala Val Ala Arg Lys Cys
 65                  70                  75                  80

Gly Tyr Pro Asn Ile Thr Cys Leu Cys Ser Thr Cys Tyr Ala Ile Asn
                 85                  90                  95

Lys Asp Ala Cys Glu Leu Leu Asn Thr Asn Asp Gly Val Arg Glu Lys
            100                 105                 110

Val Asn Ser Ile Phe Arg Glu Lys Gly Phe Asp Asp Leu Val Tyr Glu
        115                 120                 125

Lys Asp Ser Met Asn Pro Arg Thr Asn Ile Tyr His Ala Val Glu Val
    130                 135                 140

Leu Leu Ser Lys Val Glu Lys Ile Arg Glu Glu Ile Lys Phe Asp Phe
145                 150                 155                 160

Pro Gly Val Lys Ala Ala Ser His His Ala Cys His Tyr Tyr Lys Val
                165                 170                 175

Lys Tyr Leu Asp Val Ile Gly Asn Pro Glu Asn Pro Gln Leu Ile Asp
            180                 185                 190

Thr Ile Ala Glu Ala Cys Gly Ala Ser Pro Val Arg Trp Tyr Glu Asp
        195                 200                 205

Arg Thr Leu Thr Cys Gly Met Gly Phe Ser Gln Leu His Leu Asn Lys
    210                 215                 220

Ser Thr Ser Leu Gln Val Thr Lys Thr Lys Leu Asp Ser Leu Gln Arg
225                 230                 235                 240

Ala Gly Val Glu Leu Met Ile His Val Cys Pro Asn Cys His Ile Gln
                245                 250                 255

Tyr Asp Arg Tyr Gln Pro Val Ile Glu Lys Glu Phe Gly Val Glu Tyr
            260                 265                 270

Asp Met Val His Met Asn Ile Ala Gln Phe Val Ala Leu Ser Met Gly
        275                 280                 285

Ala Asp Pro Tyr Lys Val Cys Gly Phe Gln Thr His Ser Val Pro Leu
    290                 295                 300

Glu Gly Phe Leu Glu Lys Thr Gly Ile Ile
305                 310
```

<210> SEQ ID NO 7
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 7
ggatcccata tgactgacgg gctgaacaaa gct        33

<210> SEQ ID NO 8
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 8
ggatccccct cttcactccc gatgtaataa aaaaggtagc cagttc        46

<210> SEQ ID NO 9
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 9
gagaaattgc cttttgtcc atgtgtccgc agttgaactc gtc        43

<210> SEQ ID NO 10
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 10
gacgagttca actgcggaca catggacaaa aggcaattt ctc        43

<210> SEQ ID NO 11
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 11 cctttgtgt tcggaacgta tgcttttttg aaatagatcc gg        42

<210> SEQ ID NO 12
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 12
ccggatctat ttcaaaaaag catacgttcc gaacacaaaa gg        42

<210> SEQ ID NO 13
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 13
ggcatcatct ttacataggg tatcatctta tcatctctc                              39

<210> SEQ ID NO 14
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 14
gagagatgat aagatgatac cctatgtaaa gatgatgcc                              39

<210> SEQ ID NO 15
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 15
gggtatcgta ttcgtttaca tagggcatca tctttacata tgg                         43

<210> SEQ ID NO 16
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 16
ccatatgtaa agatgatgcc ctatgtaaac gaatacgata ccc                         43

<210> SEQ ID NO 17
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 17
gatatggcag ttcgggcaca tgtggatcat tagctccaca cc                          42

<210> SEQ ID NO 18
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 18
ggtgtggagc taatgatcca catgtgcccg aactgccata tc                          42

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
tactggggtt tctgggagac                                                   20

```
<210> SEQ ID NO 20
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 20
atggtcttgc tctcagcgat ga                                              22

<210> SEQ ID NO 21
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 21
aggtgttggt atgaaaatca gcaagg                                          26

<210> SEQ ID NO 22
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 22
atcagtgata gagatttcat tgggaatagt                                      30
```

US 9,598,678 B2

MICROBIAL STRAINS AND METHODS OF MAKING AND USING

CROSS REFERENCE TO RELATED APPLICATIONS

This application claims benefit under 35 U.S.C. §119(e) to U.S. Application No. 61/980,656, filed on Apr. 17, 2014.

FEDERALLY SPONSORED RESEARCH OR DEVELOPMENT

This invention was made with government support under RR017675 awarded by the National Institutes of Health. The government has certain rights in the invention.

TECHNICAL FIELD

This disclosure generally relates to microbial strains and methods of making and using.

BACKGROUND

Methane is an increasingly important global energy source, both as the primary component of natural gas and as a biologically produced fuel. Currently, Sweden uses 100% renewable methane (biogas) in place of compressed natural gas (CNG) for transportation fuel, and several European countries are implementing policies to increase their proportion of biogas transportation fuel. In addition, methane is a valuable chemical for conversion into other higher-order carbon compounds (e.g., methanol, formate, alkanes, terpenes). More than 50% of the world's methane is produced biologically by anaerobic archaea called methanogens, but one significant limitation with industrial scale biological methane production from any type of feedstock is that the rate is relatively slow.

*Methanosarcina acetivorans* is one of a unique group of organisms capable of producing methane from both acetate and methylated compounds, which are common anaerobic fermentation end products. A genetically engineered *M. acetivorans* strain is described herein that exhibits an increased rate of methane production on methanol and on acetate. Such genetically engineered microorganisms will be an essential tool in the ability to use methanogens as an inexpensive source of methane fuel derived from renewable biomass.

SUMMARY

The disclosure provides microbial strains and methods of making and using such microbial strains.

In one aspect, a HdrABC nucleic acid molecule including a mutation is provided. In some embodiments, the non-mutant HdrABC sequence is shown in SEQ ID NO:1. In some embodiments, the mutation is selected from the group consisting of a point mutation, an insertion, a deletion, and a substitution. In some embodiments, the mutant HdrABC sequence is shown in SEQ ID NO:5. In some embodiments, the nucleic acid encodes a polypeptide having an amino acid sequence shown in SEQ ID NO:6. In some embodiments, the mutation is at position 249 relative to SEQ ID NO:6. In some embodiments, the mutation is a M249V substitution.

In another aspect, a microorganism including such a nucleic acid molecule is provided. Such a microorganism can be a methanogen. In one embodiments, the microorganism is *Methanosarcina acetivorans*. In some embodiments, the nucleic acid molecule is endogenous to the microorganism. In some embodiments, the nucleic acid molecule is exogenous to the microorganism and is expressed via a construct.

In yet another aspect, a mutant HdrB polypeptide is provided. In some embodiments, the mutation includes a substitution at position 249 relative to SEQ ID NO:3. In some embodiments, the mutation includes a substitution of the methionine at position 249 relative to SEQ ID NO:3. In some embodiments, the substitution is a conservative substitution. In some embodiments, the mutant HdrB polypeptide has the sequence shown in SEQ ID NO:6.

In still another aspect, a microorganism that includes a mutant HdrB polypeptide is provided. Such a microorganism can be a methanogen. In some embodiments, the microorganism is *Methanosarcina acetivorans*. In some embodiments, the nucleic acid encoding the polypeptide is endogenous to the microorganism. In some embodiments, the nucleic acid encoding the polypeptide is exogenous to the microorganism and is expressed via a construct.

In another aspect, a method of producing methane is provided. Such a method typically includes culturing a microorganism as described herein under appropriate conditions.

In still another aspect, a method of biogas production is provided. Such a method typically includes culturing a microorganism as described herein under appropriate conditions.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
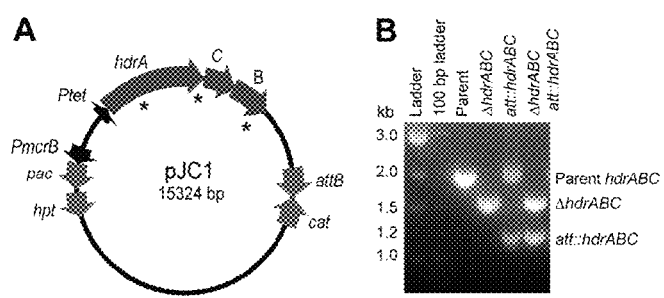
FIG. 1 shows the method of construction of plasmid pJC1 and strain verification. Panel A shows the map of plasmid pJC1 containing the *M. acetivorans* hdrABC operon under control of the P(tet) promoter. Panel B shows an agarose gel indicating PCR identification of each strain. Asterisks denote the location of point mutations in the hdrABC operon.
Figure 2:
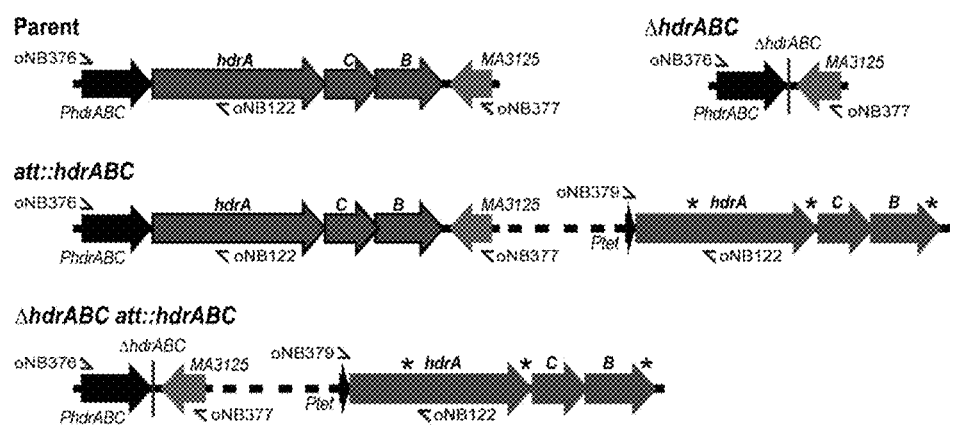
FIG. 2 shows the genomic organization of each strain, including the hdrA1C1B1 locus in the parent strain and the ΔhdrABC mutant strain before and after integration of plasmid pJC1. Blue arrows show primer binding sites. Asterisks denote the location of point mutations in the hdrABC operon.
Figure 3:
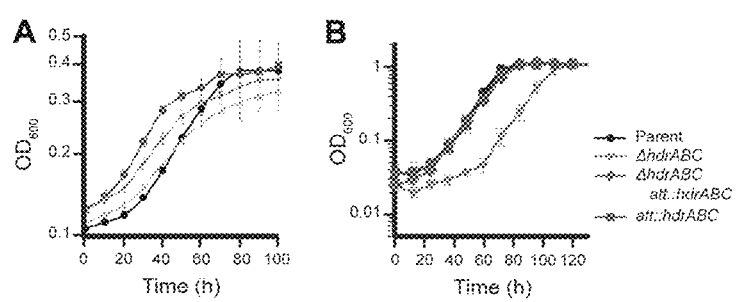
FIG. 3 are graphs showing the growth curves of strains grown in 96-well plates on methanol+acetate medium (panel A), and in sealed vessels on methanol medium (panel B). Parental strain (black circles), ΔhdrABC mutant (gray triangles), plasmid pJC1 integrated in the ΔhdrABC deletion mutant (ΔhdrABC att::hdrABC, blue diamonds), plasmid pJC1 integrated into the parent strain (att:hdrABC, red squares). Growth data was collected from triplicate biological replicates.
Figure 4:
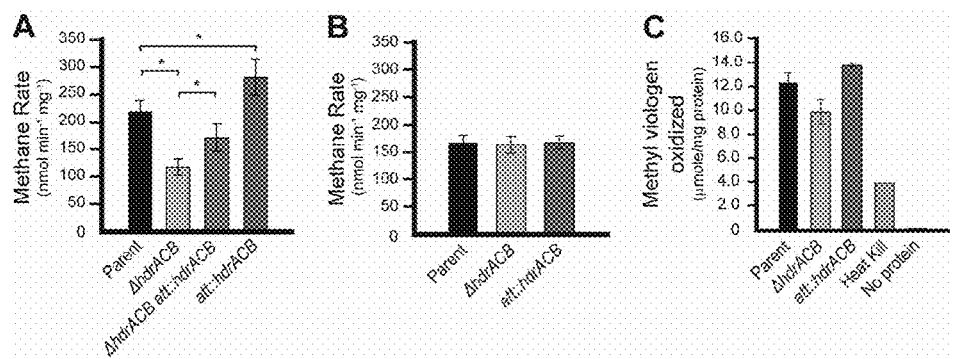
FIG. 4 are graphs showing the phenotypes of parent and hdrABC mutant strains. Rates of methane production by cell suspensions were measured from cells grown on methanol (panel A) and acetate (panel B). Methane production was measured in triplicate biological and triplicate technical replicates. Asterisks indicate p<0.0001. Panel C shows heterodisulfide reductase activity in methanol-grown cell extracts. Assays were performed in triplicate. Error bars denote the standard deviation.

A microbial strain is described herein, designated NB105, which produces methane at a significantly faster rate than the wild type strain (FIG. 1). The NB105 strain described herein also grows faster than the parent strain under certain conditions. This microbial strain represents a transformative contribution to the field of renewable methane and the production of biogas.

Attempts have been made for about thirty years to increase biogas yield but, to date, no method has been commercially successful. One problem is that the strains used in commercial-scale production facilities are not genetically tractable and the strains that have proven to be genetically tractable are, in other ways, not suitable for commercial scale production digesters. In addition, there are only a few laboratories around the world that have been able to genetically manipulate the anaerobic microbes involved. Simply by way of example, efficient genetic modification of strict anaerobic microbes requires specialized microbiology, genetics, as well as custom-built equipment. In addition, genetic modification of Methanosarcinales and Methanococcus methanogens must be performed in high osmolarity medium (e.g., containing 0.4 M sodium chloride), which is not routine. Further, the lack of commercially available co-enzymes and co-factors for anaerobes (such as co-enzyme B, co-enzyme F430, co-enzyme F420), means that the cofactors must be extracted or synthesized. Therefore, genetic investigation of biosynthetic pathways in anaerobes is prohibitively difficult. Methanogens also are not susceptible to most traditional antibiotics, so the paucity of selectable and counterselectable markers for genetically manipulating methanogens adds another layer of complexity that serves as a significant barrier to working with methanogens.

The microbial strains described herein have been designed using a specialized knowledge of the biology, genetics, and biochemistry of microbial fermentation, anaerobic digestion, and biogas production from renewable carbon feedstocks. The microbial strains described herein demonstrate that it is, in fact, possible to genetically engineer an increase in the rate and yield of biogas production in methanogens.

The HdrABC Operon

Methanogenic archaea have been divided into two categories: those that contain cytochromes and can use methanol, methyl amines, acetate, carbon monoxide, and/or $CO_2$ plus H2 as methanogenic substrates (i.e., those belonging to the order Methanosarcinales), and those that are devoid of cytochromes and can use $CO_2$ plus H2 and/or formate only to fuel anaerobic growth (i.e., those belonging to the orders Methanobacteriales, Methanomicrobiales, Methanococcales, and Methanopyrales). See, for example, Thauer, 1998, *Microbiol.*, 144:2377-406; and Wolfe, 1996, *ASM News*, 62:529-34.

In methanogens that lack cytochromes, the heterodisulfide reductase-like proteins (HDR) enzyme is soluble and composed of three subunits, HdrABC, whereas methanogens that have cytochromes have two classes of HDR enzyme: HdrABC, as in non-cytochrome containing methanogens, as well as membrane-associated HDR formed by two subunits, HdrDE. In the HdrABC enzyme, the HdrA subunit is an iron-sulfur flavoprotein, the HdrC subunit is a small iron-sulfur protein, and the HdrB subunit contains two GGC domains and harbors a special [4Fe4S] catalytic site.

The soluble HdrABC enzyme forms a complex with the soluble MvhADGHase, which then catalyzes heterodisulfide reduction in the presence of H2. This exergonic reaction is proposed to be coupled to the endergonic reduction of ferredoxin (Fd) by flavin-based electron bifurcation involving HdrA (see, for example, Thauer et al., 2008, Nat. Rev. Microbiol., 6:579-91). Flavin-based electron bifurcation (FBEB) is an important mechanism for the energy metabolism of anaerobes. A family of NADH dehydrogenases, the flavin oxidoreductase (FlxABCD, previously called FloxABCD), coupled with heterodisulfide reductase (HdrABC), both of which are widespread in anaerobic bacteria, perform FBEB in sulphate-reducing organisms.

HdrABC Nucleic Acids and Polypeptides

The nucleic acid sequence of a reference wild type HdrABC operon is shown in SEQ ID NO:1 with each of the encoded reference polypeptides shown in SEQ ID NO:2 (HdrA), SEQ ID NO:3 (HdrB), and SEQ ID NO:4 (HdrC)). As used herein, nucleic acids can include DNA and RNA, and includes nucleic acids that contain one or more nucleotide analogs or backbone modifications. A nucleic acid can be single stranded or double stranded, which usually depends upon its intended use.

Also provided are nucleic acids and polypeptides that differ from such reference sequences (e.g., SEQ ID NO:1 and SEQ ID NOs: 2, 3 and 4, respectively). Nucleic acids and polypeptides that differ in sequence from SEQ ID NO:1 and SEQ ID NOs: 2, 3, or 4, can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NO:1 and SEQ ID NOs: 2, 3, or 4, respectively. Simply by way of example, sequences that differ from SEQ ID NO:1 and SEQ ID NO:3 are shown in SEQ ID NO:5 and SEQ ID NO:6, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule, thereby leading to changes in the amino acid sequence of the encoded polypeptide. For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, a mutant HdrABC nucleic acid refers to an HdrABC operon that contains at least one mutation. A mutation can be located within any portion of the HdrABC nucleic acid operon such that any of the encoded polypeptides, HdrA, HdrB or HdrC, contain a mutation. As used herein, a mutation within HdrABC typically is a mutation that results in, for example, a conservative or non-conservative substitution; a mutation within HdrABC typically is not a null mutation (i.e., a mutation that results in the lack of expression or in a non-functional protein). A mutation in a HdrABC sequence as described herein can be contained within an endogenous HdrABC sequence or a mutation in a HdrABC sequence as described herein can be contained within an exogenous sequence (e.g., expressed/overexpressed on a construct). In addition, a mutant HdrABC sequence can be autologous (i.e., from the same species) or heterologous (i.e., from a different species) to a microorganism.

A representative HdrABC nucleic acid containing a mutation is shown in SEQ ID NO:5, and a representative HdrB protein that contains a mutation is shown in SEQ ID NO:6. In some embodiments, the mutation can at position 249 relative to the HdrB sequence shown in SEQ ID NO:3 and, for the reference sequence shown in SEQ ID NO:3, the mutation corresponds to a methionine to valine substitution (i.e., M249V). As indicated herein, however, other substitutions at that residue (e.g., residue 249 relative to SEQ ID NO:3) also would be expected to impart the same or similar phenotype (e.g., M249X). In some instances, the methionine residue at position 249 can be replaced, for example, with an alanine (M249A), an isoleucine (M249I), a leucine (M249L), or a glycine (M249G) residue. Alternatively, the methionine residue at position 249 can be replaced, for example, with a phenylalanine (M249F), a proline (M249P), a tryrosine (M249Y), or a tryptophan (M249W). It would be understood by a skilled artisan that the methionine residue at position 249 can be replaced with any of the other remaining amino acids, provided such substitutions do not result in a protein that completely lacks function and provided such substitutions impart the desired phenotype.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A construct, also referred to as a vector, containing a nucleic acid (e.g., a nucleic acid that encodes a polypeptide) also is provided. Constructs, including expression vectors, are commercially available or can be produced by recombinant DNA techniques routine in the art. A construct containing a nucleic acid can have expression elements operably linked to such a nucleic acid, and further can include sequences such as those encoding a selectable marker (e.g., an antibiotic resistance gene). A construct containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6× His tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a construct relative to a nucleic acid in such a way as to direct or regulate expression of the nucleic acid (e.g., in-frame).

A skilled artisan would appreciate that gene expression in methanogens typically requires at least one methanogen-specific expression element, since the transcriptional machinery in methanogens is a hybrid between bacterial and eukaryotic transcription systems. For example, for expression of genes in methanogens, the promoter is usually derived from another methanogen gene to ensure that the methanogen RNA polymerase and other accessory proteins needed for transcription will recognize the promoter sequences and initiate transcription. However, other expression elements such as protein transcriptional regulators and/or riboswitches from phylogenetically distant relatives (e.g., eukaryotic or bacterial) can be adapted for use in methanogen cells. See, for example, Buan et al., 2011, *Methods Enzymol.*, 494:23-42; Demolli et al., 2014, *Archea*, doi: 10.1155/2014/725610.

Constructs as described herein can be introduced into a host cell. As used herein, "host cell" refers to the particular cell into which the nucleic acid is introduced and also includes the progeny of such a cell that carry the construct. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Methods of Making Biogas

The microbial strains described herein can be used to make biogas (e.g., methane). As demonstrated herein, culturing such microbial strains under the appropriate conditions results in the production of biogas (e.g., methane). It would be appreciated by a skilled artisan that the "appropriate conditions" under which a microorganism is cultured will depend upon the particular microorganism used, and can include, without limitation, a particular culture media, the temperature at which the culture is maintained, the requirement for the presence or absence of oxygen, a particular carbon source, and/or one or more co-factors.

The microbial strains described herein can be used to make biogas (e.g., methane) at an increased rate relative to the parent strain and/or an increased amount relative to the parent strain. For example, as described herein, under corresponding culture conditions, the parent strain, NB34, produced methane at a rate of 219±18.9 nmoles min-1 mg-1, while one of the mutant strains described herein, NB105 (att::hdrABC), produced methane at a rate of 282±31.8 nmoles min-1 mg-1; this represents a 28.9% increase in rate. As used herein, an "increase" in the amount of biogas that is produced or an increase in the rate at which a biogas is produced refers to an increase (e.g., a statistically significant increase) by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 35% to about 55%, about 35% to about 50%, about 50% to about 75%, about 50% to about 85%, about 50% to about 95%, and about 75% to about 95%) relative to a corresponding microbe lacking the mutation. It would be appreciated by a person of ordinary skill in the art that, to compare a mutant microbial strain with a corresponding microbial strain lacking the mutation, culture conditions used to grow each microbial strain should be as similar as possible, referred to herein as "corresponding conditions". As used herein, statistical significance refers to a p-value of less than 0.05, e.g., a p-value of less than 0.025 or a p-value of less than 0.01, using an appropriate measure of statistical significance, e.g., a one-tailed two sample t-test.

Current practices for producing renewable methane use innocula of microbes, usually obtained from animal manure (e.g., swine or cattle manure) to digest organic carbon under anaerobic conditions. As a result, anaerobic digesters frequently fail and must be shut down, cleaned, and restarted on a regular basis. These failures represent a large cost in time, effort, wages, and lost revenue. The methods described herein can be used to increase biogas yield, require less feedstock, increase the overall rate of feedstock decomposition, reduce labor, and help stabilize production because operators would not solely rely on populations of wild microbes as the feedstock. In addition, the methods described herein require less feedstock than current methods, and anaerobic digesters would fail less often, saving plant downtime and labor costs. Thus, the methods described herein can significantly reduce the costs involved with the production of biogas.

In some embodiments, a live culture of the microbial strain described herein is added (e.g., inoculated) to a digester at regular intervals. In some embodiments, the microbial strains described herein can be provided in, for example, a lyophilized or dehydrated form. One of the advantages of the microbial strain described herein is that, because it is anaerobic, in the absence of very particular growth conditions, microbes from the microbial strain described herein will not survive. This feature significantly reduces the possibility of unintentional release into the environment.

Additional mutations can be introduced into the microbial strain described herein to further increase biogas production or to increase other features of the strain such as, for example, yield, increased growth rate, the ability to use novel substrates, or resistance to oxidative stress. The microbial strain described herein also can be a part of a microbial consortia (e.g., a microbial community that has evolved together) to be able to efficiently convert various renewable feedstocks to methane and/or additional fermentation co-products.

Biogas made by the methods described herein can be used, without limitation, for renewable energy, compressed biogas/natural gas for transportation, microbial fermentation or respiration (bioorganic catalysis), or any other technology that uses methane or biogas including (in)organic catalytic synthesis technologies.

Further, a mutant HdrABC nucleic acid sequence as described herein can be introduced into other microbial organisms having industrial or biotechnological utility in order to alter those strains. HdrABC homologs and orthologs are found in the genomes of non-methanogenic archaea and bacteria, such as members of the genus *Metallosphaera*, *Archaeoglobus*, sulfate-reducing bacteria (including, but not restricted to, *Desulfovibrio*, *Desulfotomaculum*), *Moorella*, *Aquifex*, *Sulfolobus*, *Carboxydothermus*, *Pelotomaculum*, *Chlorflexi* (including, but not restricted to, *Chloroflexus*, *Chlorobium*), syntrophs (including, but not restricted to, *Syntrophomonas*), and metal-reducing or metal-oxidizing microbes such as *Geobacter*, and could be mutated (or a mutant sequence overexpressed) in any of such species The above-mentioned mutant species can be used for bioremediation or metal bioleaching, aerobic or anaerobic fermentations (including gas fermentation), and production of biofuel cells, and would exhibit increased rate and yield of fermentation and/or respiration.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Materials and Methods

Cell growth curves were determined by monitoring the optical density (OD) of the cells in culture over time. The OD of the cells was determined using two methods as indicated: (1) using growth in Balch tubes and obtaining the OD manually every 4 hours for 3-7 days using a Spectronic 20 D+ spectrophotomter ("BT+Spec 20"), where; or (2) using an anaerobic plate reader and obtaining the OD automatically every 2 hours. For biomass measurements of each strain, ten cultures (10 ml) were grown to stationary phase on HS medium containing 125 mM MeOH. Methane in the headspace was measured as described below, and cells were collected on pre-weighed 0.2 µm nylon filters by vacuum. Filters were dried at 95° C. and weighed daily until weights stabilized and remained consistent for three days. Uninoculated medium was used as a blank.

The amount and rate of methane production was determined using gas chromatography (GC). For methane endpoint assays, 10 ml cultures were grown in 125 mM methanol HS medium to stationary phase, and 100 µl headspace samples were transferred to empty, crimped 2 ml serum vials using a gastight Hamilton syringe. For cell suspension assays, cells were grown with appropriate carbon source to an OD(600) of between 0.3 and 0.5 (exponential growth) and put on ice. Under strict anaerobic conditions, cells from 10 ml culture were harvested, pelleted by centrifugation, and washed twice in HS media without a carbon source. Cells were resuspended in 0.5 ml HS media with 50 µM mupirocin to halt protein synthesis, then aliquoted into 2 ml serum vials containing HS+125 mM MeOH or 120 mM acetate in replicates of 5. Serum vials were sealed with aluminum crimps and warmed for 5 minutes at 35° C. to start the assay. Methane in the headspace was measured via flame ionization on an Agilent 7890 Gas Chromatograph with a GS CarbonPLOT column at 145° C. using an auto injector.

The amount of HdrABC enzyme activity was measured by biochemical assay. Coenzyme M was purchased from Sigma-Aldrich (St. Louis, Mo.). Coenzyme B and CoM-S-S-CoB was synthesized in-house (Welte and Deppenmeier, 2014, Biochim. Biophys. Acta., 1837:1130-47). Cells were grown to early stationary phase (OD(600) of 1.0) in HS supplemented with 125 mM MeOH. Under strict anaerobic conditions, 30 ml of cell cultures were harvested, pelleted by centrifugation, and washed twice with 10 ml 0.1 M NaPO$_4$, 0.4 M NaCl (pH 8.0). Cells were lysed osmotically by addition of 3 ml 0.1 M NaPO$_4$ (pH 8.0) without NaCl. Protease inhibitor cocktail (Thermo Pierce) was added, and the lysate was centrifuged at 22,000×g for one hour to pellet cell debris and membranes. The concentration of soluble cytoplasmic protein in the resulting extract was measured via Bradford assay against a 2 mg BSA standard (Thermo Pierce). Hdr assays (Welte and Deppenmeier, 2014, supra) were modified for a 96-well plate format. Briefly, reactions were prepared with 170 µl 0.1 M NaPO$_4$ (pH 8.0), 28 µl extract and 2 µl methyl viologen. The reaction was began with the addition of 30 µl CoM-CoB heterodisulfide, and the increase in oxidized methyl viologen was followed at 578 nm in a Tecan Sunrise plate reader at 35° C.

Example 2

General Description of Strain Construction

To generate the ΔhdrABC strains, the hdrABC sequence was mutated using site-directed mutagenesis and overlapping PCR. Primers and DNA sequences in Table 2 were designed using Vector NTI software (Invitrogen). Genes, oligos, and multiple cloning sites were synthesized commercially by IDT and Invitrogen. To overexpress hdrACB, the operon (MA3126-3128) was amplified from the *M. acetivorans* chromosome (strain NB34) using primers oNB68, oNB69, and oNB72-81 (listed in Table 2). Primers oNB72-oNB81 introduced five point mutations to remove five NdeI restriction sites from the hdrACB operon. The resulting fused PCR product contained BamHI restriction sites at the 5' and 3' ends, as well as an NdeI site preceding the start codon of the hdrA gene. The PCR product was ligated into plasmid pNB708, creating pNB709, and verified by restriction digest and sequencing. The mutated hdrACB operon was amplified from pNB709 using oligos oNB68 and oNB69, and ligated into pJK027A at the NdeI and BamHI restriction sites to create plasmid pJC1 (Table 1). The hdrABC operon is under control of the PmcrB(tetO1) (aka Ptet) promoter. The Ptet promoter is constitutive when transformed into strains lacking the tetR repressor gene, but can be controlled by addition of tetracycline in strains that express TetR repressor. *M. acetivorans* was transformed with pJC1 as previously described (Buan and Metcalf, 2010, Mol. Microbiol., 75:843-53). Transformants were verified via PCR screen for wild type hdrABC, the ΔhdrABC operon deletion, and Ptet hdrABC (in pJC1) using primers listed in Table 2. Various PCR techniques were employed to create methanophenazine mutant strains (listed in Table 1), including overlap extension and site-directed mutagenesis.

For all PCR reactions, Phusion Flash PCR Master Mix was used as a source of proofreading DNA polymerase (Thermo Scientific). DNA purification was carried out using Wizard kits from Promega (Madison, Wis.). DNA fragments were joined using T4 DNA Ligase (New England Biolabs) or GeneArt kits (Invitrogen). Restriction enzymes (AscI, BamHI, NdeI, NcoI, EcoRI, SphI, XbaI) were purchased from New England Biolabs (Ipswich, Mass.). All plasmids were sequenced by Eurofins Operon MWG (Huntsville, Ala.).

After purification from *E. coli*, the plasmids were transfected into *M. acetivorans* using liposome-mediated transfection (using the DOTAP liposome transfection reagent from Roche), and the operon was recombined into the genome. Colonies then were selected for puromycin resistance (from the puromycin acetyltransferase cassette included on the pJC1 vector). Certain of the strains and their genotype are provided in Table 1.

TABLE 1

Strains and Genotypes

*E. coli* strains

| NB # | Genotype | Purpose | Source |
|---|---|---|---|
| 3 | F' proA+B+ laclq Δ(lacZ)M15 zzf::Tn10 (TetR)/fhuA2Δ(argF-lacZ)U169 phoA glnV44 Φ80Δ(lacZ)M15 gyrA96 recA1 endA1 thi-1 hsdR17 | 5α F' lacl$^q$. Replication of pNEB193 derived plasmids. | New England Biolabs |
| 10 | F- mcrA Δ(mrr-hsdRMS-mcrBC) φ80lacZΔM15 ΔlacX74 recA1 araD139 Δ(ara-leu) 7697 galU galK rpsL (StrR) endA1 nupG λ- att::Prha trfA33-254D | DH10B att::pAMG27. Replication of oriV copy-control plasmids. High copy replication is induced by addition of rhamnose. | Guss A M, et al. 2008 | pNEB193 derivative plasmids

| NB # | Genotype | Purpose | Plasmid name | Source |
|---|---|---|---|---|
| 13 | pUC ori, bla+ | *E. coli* cloning | pNEB193 | New England Biolabs |

TABLE 1-continued

Strains and Genotypes

| NB # | Genotype | | Plasmid name | Source |
|---|---|---|---|---|
| 47 | pUC ori, bla+, NcoI | adds NcoI site to pNEB193 | pNB708 | This study |
| 48 | pUC ori, bla+, hdrABC | *M. acetivorans* NdeI hdrA1C1B1 operon (with all internal NdeI sites removed) cloned into the BamHI site | pNB709 | This study | pJK027A derivative plasmids

| NB # | Genotype | Purpose | Plasmid name | Source |
|---|---|---|---|---|
| 53 | oriV, repE, sopABC, cat, φC31 attB, Pmcr (*M. voltae*) pac-hpt, PtetO1 uidA | Integration at φC31 attP site | pJK027A | Guss A M, et al. 2008 |
| 83 | PtetO1 hdrABC | Constitutive overproduction and complementation of HdrABC protein in *Methanosarcina*. Tetracycline-controlled expression of HdrABC in tetR+ *Methanosarcina* strains. | pJC1 | This study |

*Methanosarcina acetivorans* C2A strains

| NB # | Genotype | Purpose | | Source |
|---|---|---|---|---|
| 34 | Δhpt::φC31 int, attP | Parental strain | | same as WWM82 |
| 36 | ΔhdrACBΔΔhpt::φC31 int, attP | ΔhdrABC mutant | | same as WWM287 |
| 105 | Δhpt::φC31 int, att::pJC1 | Effect of constitutive overproduction of HdrABC. att::hdrABC | | This study |
| 106 | ΔhdrACB Δhpt::φC31 int, att::pJC1 | Complementation of ΔhdrABC by pJC1. ΔhdrABC att::hdrABC | | This study |

Example 3

Construction of the NB105 Strain

The hdrABC genes (MA3126-3128; see Galagan et al., 2002, Genome Res., 12:532-42; see, also, GenBank Accession No. AE010299) were amplified from the *M. acetivorans* chromosome (strain NB34, propagated from *M. acetivorans* strain, WWM82, from Dr. Metcalf's Lab, University of Illinois, Urbana-Champaign on July 2010) chromosome using primers oNB68, oNB69, oNB72-81 (see Table 2). The listed oligos simultaneously amplify the hdrABC operon and create mutations that remove internal NdeI restriction sites (the wild-type operon contains five) and results in a PCR product that has a BamHI restriction site after the stop codon on the 3' end of the operon.

The mutated hdrABC operon then was cloned into the *E. coli* plasmid, pNB708, at the BamHI site. pNB708 was produced using oligos, oNB60 and oNB61 (see Table 2), to amplify plasmid, pNEB193 (purchased from New England Biolabs). The resulting PCR product was digested with Dpn1 and transformed into *E. coli* strain, NB3 (New England Biolabs), to produce plasmid, pNB708, which has a new NcoI site in the plasmid. The *E. coli* strain carrying pNB708 was designated NB47.

The resulting plasmid, pNB709, carried in *E. coli* strain, NB48, was used as a template in subsequent PCR reactions to amplify the mutated hdrABC operon with oligos, oNB68 and oNB69 (see Table 2). The mutated hdrABC operon was cloned into pJK027A at the NdeI and BamHI sites to produce plasmid pJC1. pJC1 contains a φC31 attP site, and, in the presence of φC31 recombinase, is inserted into any DNA containing the φC31 attB site. pJC1 also contains a mutated hdrABC operon driven by the PtetO1 promoter, which is transcribed constitutively in *Methanosarcina* species unless the parent strain expresses a TetR repressor protein, in which case, HdrABC expression is rendered tetracycline-inducible by TetR binding to the tetO1 operator site on the promoter. pJC1 was transformed into NB34 to create strain NB105, in which pJC1 has recombined into the *M. acetivorans* (NB34) chromosome at the hpt locus. In cell-suspension assays with methanol, strain NB105 produced methane at a rate that was 35% faster than that of the NB34 parent strain.

TABLE 2

Oligonucleotide Sequences

| oNB# | Purpose | Sequence (5'-3') | SEQ ID NO: |
|---|---|---|---|
| | hdrABC primers | | |
| 68 | *M. acetivorans* BamHI NdeI hdrABC BamHI fwd | GGATCCCATATGACTGACGGGCTGAACAAAGCT | 7 |
| 69 | *M. acetivorans* BamHI NdeI hdrABC BamHI rev | GGATCCCCCTCTTCACTCCCGATGTAATAAAAAAGGTAGCCAGTTC | 8 |
| 72 | removes NdeI site 1 fwd | GAGAAATTGCCTTTTTGTCCATGTGTCCGCAGTTGAACTCGTC | 9 |
| 73 | removes NdeI site 1 rev | GACGAGTTCAACTGCGGACACATGGACAAAAAGGCAATTTCTC | 10 |
| 74 | removes NdeI site 2 fwd | CCTTTTGTGTTCGGAACGTATGCTTTTTTGAAATAGATCCGG | 11 |
| 75 | removes NdeI site 2 rev | CCGGATCTATTTCAAAAAAGCATACGTTCCGAACACAAAAGG | 12 |
| 76 | removes NdeI site 3 fwd | GGCATCATCTTTACATAGGGTATCATCTTATCATCTCTC | 13 |
| 77 | removes NdeI site 3 rev | GAGAGATGATAAGATGATACCCTATGTAAAGATGATGCC | 14 |
| 78 | removes NdeI site 4 fwd | GGGTATCGTATTCGTTTACATAGGGCATCATCTTTACATATGG | 15 |
| 79 | removes NdeI site 4 rev | CCATATGTAAAGATGATGCCCTATGTAAACGAATACGATACCC | 16 |
| 80 | removes NdeI site 5 fwd | GATATGGCAGTTCGGGCACATGTGGATCATTAGCTCCACACC | 17 |
| 81 | removes NdeI site 5 rev | GGTGTGGAGCTAATGATCCACATGTGCCCGAACTGCCATATC | 18 |

TABLE 2-continued

Oligonucleotide Sequences

| oNB# | Purpose | Sequence (5'-3') | SEQ ID NO: |
|---|---|---|---|
| 122 | hdrA: amplifies within inside both parent and insert hdrA. | TACTGGGGTTTCTGGGAGAC | 19 |
| 376 | identify hdrABC deletion: amplifies 5' upstream of MA3128 | ATGGTCTTGCTCTCAGCGATGA | 20 |
| 377 | identify hdrABC deletion: amplifies 3' downstream of MA3126 | AGGTGTTGGTATGAAAATCAGCAAGG | 21 |
| 379 | identify Ptet hdrABC insert | ATCAGTGATAGAGATTTCATTGGGAATAGT | 22 |

Example 4

Evaluation of Strains

The growth kinetics of the strains indicated above in Table 1 were used to evaluate the growth phenotypes of each strain on methanol, methanol+acetate, or acetate substrates, using Method (1) described above ("BT+Spec20"), and the results are shown in Table 3.

TABLE 3

Culture Doubling Time for Adapted Cells (Hours)

| | Growth Substrate | | | | | | | | | | | |
|---|---|---|---|---|---|---|---|---|---|---|---|---|
| | MeOH | | | | MeOH + Acetate | | | | Acetate | | | |
| Strain | hours | Std dev | p vs Parent | p vs ΔhdrABC | hours | Std dev | p vs Parent | p vs ΔhdrABC | hours | Std dev | p vs Parent | p vs ΔhdrABC |
| Parent | 8.5 | ±0.17 | 1 | 0.0000 | 9.4 | ±0.28 | 1 | 0.0046 | 44.0 | ±2.80 | 1 | 0.0000 |
| att::hdrABC | 8.4 | ±0.11 | NS | 0.0001 | 9.7 | ±0.16 | NS | NS | 47.6 | ±2.64 | NS | 0.0003 |
| ΔhdrABC att::hdrABC | 9.1 | ±0.14 | 0.0012 | 0.0010 | 10.3 | ±0.48 | NS | NS | 58.0 | ±3.05 | 0.0002 | NS |
| ΔhdrABC | 9.9 | ±0.24 | 0.0000 | 1 | 10.1 | ±0.20 | 0.0046 | 1 | 61.8 | ±2.94 | 0.0000 | 1 |

Cells were adapted to methanol for 25 generations. Data were collected from five biological replicates (N = 5). Significance p values determined by unpaired Student's t-test.
NS: not significant, $p > 0.01$.

The strains indicated above in Table 1 were used to evaluate the production of methane from methanol or acetate using Method (1) described above (methane production and biomass measurements), and the results are shown in Table 4.

TABLE 4

Growth Yield and Methane Yield

Biomass

| Strain | g mol$^{-1}$ | Std dev | p vs Parent |
|---|---|---|---|
| Parent | 7.295 | 0.7378 | 1 |
| att::hdrABC | 6.977 | 0.6565 | NS |
| ΔhdrABC att::hdrABC | 7.020 | 0.7550 | NS |
| ΔhdrABC | 8.634 | 0.5642 | 0.0081 |

TABLE 4-continued

Growth Yield and Methane Yield

Methane

| Strain | mmoles l$^{-1}$ | Std dev | p vs Parent |
|---|---|---|---|
| Parent | 95.0 | 3.66 | 1 |
| att::hdrABC | 95.7 | 1.77 | NS |
| ΔhdrABC att::hdrABC | 95.9 | 2.62 | NS |
| ΔhdrABC | 97.6 | 3.71 | NS |

Cells were adapted to methanol for 25 generations. Data were collected from ten biological replicates (N = 10). Significance p values determined by unpaired Student's t-test. NS: not significant, $p > 0.01$. Theoretical methane yield: 93.75 mmoles l$^{-1}$.

Example 5

Evaluating the Substrate Specificity of HdrABC

As shown in Table 3, acetate resolves the phenotype produced by overexpression of HdrABC. Since these results suggest that HdrABC is specific for growth on methylotrophic substrates (with chemical formula of CH3-X, where X represents any element except carbon), experiments were performed to determine if HdrABC uses an electron donor produced in acetate-grown cells. To make this determination, the rates of methane production on acetate substrates with or without methanol are measured, suggesting that HdrABC is lacking the appropriate electron donor in acetate-grown cells.

Example 6

Evaluating the Role of Electron Bifurcation

Figure 5:
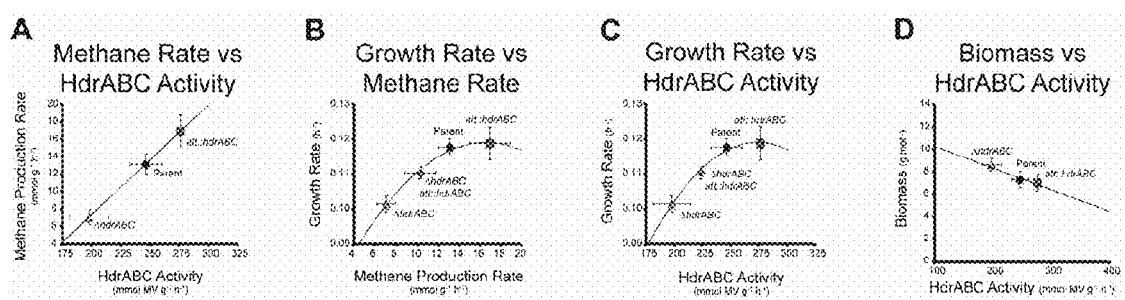
FIG. 5 shows the correlative relationships between HdrABC expression level and methane rate, growth rate, and total biomass synthesis. Panel A shows that the rate of methane production is directly dependent on the amount of HdrABC enzyme activity in the cell ($R^2$ correlation coefficient of 1.00). Panel B shows the second-order relationship between growth rate and methane production rate ($R^2$ correlation coefficient of 0.981). Panel C shows the second-order relationship between growth rate and HdrABC enzyme activity ($R^2$ correlation coefficient of 0.990). Panel D shows HdrABC enzyme activity has a strong negative correlation with total biomass synthesis ($R^2$ correlation coefficient of 0.959). Error bars denote the standard deviation.

As shown in FIG. 5, altering HdrABC enzyme activity in the cells affects the rate of growth, the rate of methane production, and the amount of biomass that is produced. The amount of HdrABC activity has a direct positive correlation with the rate of methane produced from methanol ($R^2=1.00$). The rate of growth and methane rate have a second-order correlation ($R^2=0.99$). The rate of growth also is correlated to the rate of HdrABC activity by a second-order relationship ($R^2=0.99$). Finally, the amount of biomass has a direct negative correlation with the amount of HdrABC activity ($R^2=0.974$).

Figure 6:
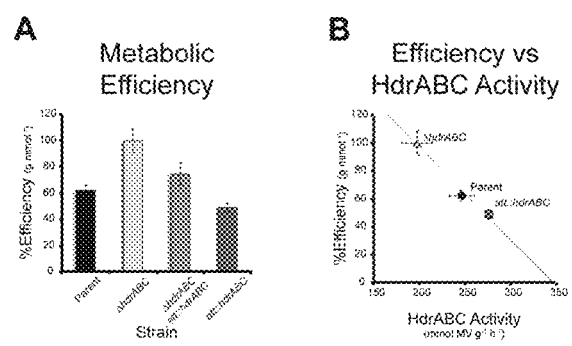
FIG. 6 shows the mechanism of methane rate improvement in the hdrABC overexpressing strain. Panel A shows the metabolic efficiency of each strain. Values are normalized to the ΔhdrABC mutant strain. Panel B shows a strong negative correlation between HdrABC enzyme activity and metabolic efficiency ($R^2=0.961$). Error bars denote the standard deviation.

As shown in FIG. 6, the effect of HdrABC expression on *Methanosarcina* is to decrease the metabolic efficiency of the organism, i.e., more substrate is channeled to methane production at the expense of biomass synthesis. Metabolic efficiency is defined by the equation:

$$\% \, e = \frac{k_g}{k_{CH_4}} \times 100$$

Where $k_g$ is defined as the growth rate and $k_{CH_4}$ is defined as the rate of methane production. The level of HdrABC activity and the % e have a direct negative correlation ($R^2=0.98$).

Example 7

Sequences

```
Mac hdrABC (forward)
                                                       (SEQ ID NO: 1)
atgactgacg ggctgaacaa agctgccgta tttatctgcc actgcagcgg gaatatttcc gaacatgttg atattgatgc cgtgaaaaaa acccttaagg cagaagggat ttcggttttt gattatgagt acatgtgctc aagtcaggga caggctctta ttaaaaagaa gattgtggag gggagcctgg acagggtggt aataggttca tgcactccat ccaaacacgg tactctcttt aaaaagtgca tacaggaaac cggtttgaac agggcagggc ttgaaattgc aaatctcagg gaacaatgtg cctgggtgca ccctgaccgg accggagcta cagaaaaagc tctttccctc ctgagggcca aactcaaacg cctggaaaat gtagagcccc tggatgaaat caaagtcgat atcgctcagc aggcccttgt tatcggtggg ggaatagcag gaattacggc tgcactgaac cttgcagata acggagtttc cactgttctt gttgagaata actcaagcat aggcgggcag atggcaaaaa tcgggaagat attttccccg gacaagcttg ctgaagaatg tgcaatgtgc tctctcagtc ctctgatgaa tgaggttgca gcccacccga aaattacact tttgacccgg accgaagttg aaagcctgag cgggagcgca ggaaacttta cgatcaggct aaggaaaaag ccaagatacg tcaaagacag ctgtacggca tgcgggaggt gcagccgggt ctgtccagtc caggttgaag acgagttcaa ctgcggacat atggacaaaa aggcaatttc tcttcgcttc tcccagtcag tccccaagat ctactgtatt gatcccgatt attgccttca gctgaatggt gaagcctgcg gaaaatgtgc ggatgcctgt aaaaacgaag caattgactt ttcccagaag gaagagatcg ttgaacttaa cgtgggggca gttgttgttg ccaccgggtt tgaggagtat gacgtctccc agaaacccca gtacggatac gggattttcg aaaacgtgct gacccagatg gaacttgcca gagttcttgg catcaatggc cctacaaaag gagaactcct gagagtctca gatttcagca aagcttccag cgatcctacc cctgcaacct gtgattcaag gtgcgaagat tcatctgatg aatcccaagg taccgacacg ccaaaaagaa tagtcatgat ccagtgtgtg ggatcaaggg atgaaaaaga aggggggaaac cgctactgtt ccagatactg ctgcatggca gctctgaaac atgcaagcct gattaagaaa aaacatccgg aaacggaaat cacgatttgc tacattgatg tcagggcttt tggtttctat gaaaattatt accgcgcagt tcaggagacc ggagtcaact ttgtgcgggg aaggcctgcc gaagttattg aaaagccgga taagagcctt gttgtaagag tcgaggatac ccttgaccag aaaatgaggg aacttcctgc cgaccttgtt
```

-continued

```
gtgctttccg cagcaatggt gccttctccc gggaccagga aaattgccag tgtgctgaac ctgagccagg atgaaagcgg ctttatcaag gaaaggcact ccaagctgaa acccgtggac agttcccttg acggaatctt tgtctgcggc actgcccaga gccccaagga cgttaccgat accattgccc aggcaggact tgcagccgta agggcaaggg ctttcattac ggacagcccg aaggtgctgg ataatgaaat tgcgaccatt aaccagttgc tctgcacgcg ctgcggagaa tgccttaaat gccccttcga tgccctctcc gtaaatgaga gcggaagggt agtgcttgac ccgcttatct gcacaggctg cggatactgt accaagctct gcggagaagg agccgtccag atcgcaggct ttacgaaact ccagctgaaa gccgagatgg agggtgtgct cgaagaaggg gatgtgctcg gctttgtaaa cagcgggatt gcttcccctta cctgtgacaa tatcggtaac agtgtgctta cttacccttc gaatgtcaaa ttgataaagg tcccgaccgg ccttgtagtg gacagagacc tggtgctgca cgccttcagg cacgggcgt cttctgtcct ttttgtagag gacccaccag acaacccgag ggctgaggtg atatatcctc ttactgtcag ccactttgag gaactcaaag aggaacttgg agattcagga aaccggatct atttcaaaaa agcatatgtt ccgaacacaa aagggcttgc aggaactttc accagccttg cccgggaagg agagatgata agatgatacc atatgtaaag atgatgccat atgtaaacga atacgatacc ccggagtgta aaactcttgc agagaccgca aagaaaagta tccgaacccc tgagtccctc ggactggacc gctgtatcca gtgcggagcc tgcactgctt cctgtcctgc agcccggttt acggactaca gcccccgaca gatcgtaaaa aaagtgctcg aaaatgatcg cagtgtgctt gaatccgaaa tgatctggtc ctgcttctac tgctattcct gcaatttgcg ctgtcccagg aacaacagcc ccgtaacaat cgtgcaggtt ctccggcaga tggctatcaa cgaaggaatc agggttgaaa agcttgccta tttccttgag atcggagagc acctcggaga aaacggagcc agcaaggttc cgggcgctgg catcaaaaac atggaaaaag accttggaga acgctggatt ggaattaaaa ggaagctgga accaatacgt tccgaacttg ggctcagtgc cagggatgtc aggaacaccc atggagaggt tcaggctatt cttgagagca cgggctattt cgaaagggaa aagtggatca aagcaagggt ccaggaaaag ggaatccggg gttttctgaa gacggaccgc acagggacat cctgcactga aaagaagaaa aacagcggag acttaggctt tgaaagcgat agagagtata ccggacagga agctcttact gtttaagagc tgcatggtcg ggcaggaata ccccggaatc gaaacagcca ccagttacgt gtttgaccgg cttgggggtag attactgcat aaacgacgag cagtcctgct gtacaggaat aggccactat accgatgtct ttgaagggct cacaacagcc gccattgcag cccggaactt tgccgtcgcc agaaagtgcg ggtacccgaa cattacctgc ctctgttcaa cctgttatgc cataaacaag gacgcatgcg aactccttaa caccaacgat ggggtccggg aaaaagtcaa ctccatcttc cgggaaaaag gctttgatga ccttgtctat gaaaaggact ccatgaaccc cagaaccaat atctatcacg cagtcgaggt cctcctgagc aaagtcgaaa agatccggga agagataaag ttcgatttcc ccggcgttaa agcagcctct catcacgcct gccactatta taaagtcaaa taccttgacg taatcggaaa ccccgaaaac ccccagctta tagacacgat agccgaagcc tgcggggcat cccctgtgcg ctggtacgaa gatcgaaccc tcacctgcgg aatgggcttt tcccagctcc acctcaataa agcacctct ctccaggtta ccaaaacaaa acttgacagc ctccagagag ccggtgtgga gctaatgatc catatgtgcc cgaactgcca tatccagtac gaccgctacc agcccgttat cgaaaaagag ttcgggggttg agtacgacat ggtgcacatg aacattgccc agttcgtagc cctctcaatg ggagcagacc cctacaaagt atgcggtttc cagactcact ccgtgcctct ggaaggattt
```

-continued

```
cttgaaaaga ccggaataat ataatgtcca gtttcaaagt agaactggct accttttta
ttacatcggg agtgaagagg g
```

Mac hdrA protein (SEQ ID NO: 2)

```
MTDGLNKAAV FICHCSGNIS EHVDIDAVKK TLKAEGISVF DYEYMCSSQG QALIKKKIVE
GSLDRVVIGS CTPSKHGTLF KKCIQETGLN RAGLEIANLR EQCAWVHPDR TGATEKALSL
LRAKLKRLEN VEPLDEIKVD IAQQALVIGG GIAGITAALN LADNGVSTVL VENNSSIGGQ
MAKIGKIFSP DKLAEECAMC SLSPLMNEVA AHPKITLLTR TEVESLSGSA GNFTIRLRKK
PRYVKDSCTA CGRCSRVCPV QVEDEFNCGH MDKKAISLRF SQSVPKIYCI DPDYCLQLNG
EACGKCADAC KNEAIDFSQK EEIVELNVGA VVVATGFEEY DVSQKPQYGY GIFENVLTQM
ELARVLGING PTKGELLRVS DFSKASSDPT PATCDSRCED SSDESQGTDT PKRIVMIQCV
GSRDEKEGGN RYCSRYCCMA ALKHASLIKK KHPETEITIC YIDVRAFGFY ENYYRAVQET
GVNFVRGRPA EVIEKPDKSL VVRVEDTLDQ KMRELPADLV VLSAAMVPSP GTRKIASVLN
LSQDESGFIK ERHSKLKPVD SSLDGIFVCG TAQSPKDVTD TIAQAGLAAV RARAFITDSP
KVLDNEIATI NQLLCTRCGE CLKCPFDALS VNESGRVVLD PLICTGCGYC TKLCGEGAVQ
IAGFTKLQLK AEMEGVLEEG DVLGFVNSGI ASLTCDNIGN SVLTYPSNVK LIKVPTGLVV
DRDLVLHAFR HGASSVLFVE DPPDNPRAEV IYPLTVSHFE ELKEELGDSG NRIYFKKAYV
PNTKGLAGTF TSLAREGEMI R*
```

Mac hdrB protein (SEQ ID NO: 3)

```
LKAIESIPDR KLLLFKSCMV GQEYPGIETA TSYVFDRLGV DYCINDEQSC CTGIGHYTDV
FEGLTTAAIA ARNFAVARKC GYPNITCLCS TCYAINKDAC ELLNTNDGVR EKVNSIFREK
GFDDLVYEKD SMNPRTNIYH AVEVLLSKVE KIREEIKFDF PGVKAASHHA CHYYKVKYLD
VIGNPENPQL IDTIAEACGA SPVRWYEDRT LTCGMGFSQL HLNKSTSLQV TKTKLDSLQR
AGVELMIHMC PNCHIQYDRY QPVIEKEFGV EYDMVHMNIA QFVALSMGAD PYKVCGFQTH
SVPLEGFLEK TGII*
```

Mac hdrC protein (SEQ ID NO: 4)

```
MIPYVKMMPY VNEYDTPECK TLAETAKKSI RTPESLGLDR CIQCGACTAS CPAARFTDYS
PRQIVKKVLE NDRSVLESEM IWSCFYCYSC NLRCPRNNSP VTIVQVLRQM AINEGIRVEK
LAYFLEIGEH LGENGASKVP GAGIKNMEKD LGERWIGIKR KLEPIRSELG LSARDVRNTH
GEVQAILEST GYFEREKWIK ARVQEKGIRG FLKTDRTGTS CTEKKKNSGD LGFESDREYT GQEALTV*
```

Mac hrABC (forward - mutated)

(SEQ ID NO: 5)

```
atgactgacg ggctgaacaa agctgccgta tttatctgcc actgcagcgg gaatatttcc
gaacatgttg atattgatgc cgtgaaaaaa acccttaagg cagaagggat ttcggttttt
gattatgagt acatgtgctc aagtcaggga caggctctta ttaaaaagaa gattgtggag
gggagcctgg acagggtggt aataggttca tgcactccat ccaaacacgg tactctcttt
aaaaagtgca tacaggaaac cggttttgaac agggcagggc ttgaaattgc aaatctcagg
gaacaatgtg cctgggtgca ccctgaccgg accggagcta cagaaaaagc tcttcccctc
ctgagggcca aactcaaacg cctggaaaat gtagagcccc tggatgaaat caaagtcgat
atcgctcagc aggcccttgt tatcgtgggg ggaatagcag gaattacggc tgcactgaac
cttgcagata acgagttttc cactgttctt gttgagaata actcaagcat aggcgggcag
atggcaaaaa tcgggaagat atttccccg acaagcttg ctgaagaatg tgcaatgtgc
tctctcagtc ctctgatgaa tgaggttgca gcccacccga aaattacact tttgacccgg
```

-continued

```
accgaagttg aaagcctgag cgggagcgca ggaaacttta cgatcaggct aaggaaaaag ccaagatacg tcaaagacag ctgtacggca tgcgggaggt gcagccgggt ctgtccagtc caggttgaag acgagttcaa ctgcggacac atggacaaaa aggcaatttc tcttcgcttc tcccagtcag tccccaagat ctactgtatt gatcccgatt attgccttca gctgaatggt gaagcctgcg gaaaatgtgc ggatgcctgt aaaaacgaag caattgactt ttcccagaag gaagagatcg ttgaacttaa cgtgggggca gttgttgttg ccaccgggtt tgaggagtat gacgtctccc agaaacccca gtacggatac gggattttcg aaaacgtgct gacccagatg gaacttgcca gagttcttgg catcaatggc cctacaaaag agaactcct gagagtctca gatttcagca aagcttccag cgatcctacc cctgcaacct gtgattcaag gtgcgaagat tcatctgatg aatcccaagg taccgacacg ccaaaaagaa tagtcatgat ccagtgtgtg ggatcaaggg atgaaaaaga aggggaaac cgctactgtt ccagatactg ctgcatggca gctctgaaac atgcaagcct gattaagaaa aacatccgg aaacggaaat cacgatttgc tacattgatg tcagggcttt tggtttctat gaaaattatt accgcgcagt tcaggagacc ggagtcaact ttgtgcgggg aaggcctgcc gaagttattg aaaagccgga taagagcctt gttgtaagag tcgaggatac ccttgaccag aaaatgaggg aacttcctgc cgaccttgtt gtgctttccg cagcaatggt gccttctccc gggaccagga aaattgccag tgtgctgaac ctgagccagg atgaaagcgg ctttatcaag gaaaggcact ccaagctgaa acccgtggac agttcccttg acggaatctt tgtctgcggc actgcccaga gccccaagga cgttaccgat accattgccc aggcaggact tgcagccgta agggcaaggg cttcattac ggacagcccg aaggtgctgg ataatgaaat tgcgaccatt aaccagttgc tctgcacgcg ctgcggagaa tgccttaaat gccccttcga tgccctctcc gtaaatgaga gcggaagggt agtgcttgac ccgcttatct gcacaggctg cggatactgt accaagctct gcggagaagg agccgtccag atcgcaggct ttacgaaact ccagctgaaa gccgagatgg agggtgtgct cgaagaaggg gatgtgctcg gctttgtaaa cagcgggatt gcttcccta cctgtgacaa tatcggtaac agtgtgctta cttacccttc gaatgtcaaa ttgataaagg tcccgaccgg ccttgtagtg gacagagacc tggtgctgca cgccttcagg cacggggcgt cttctgtcct ttttgtagag gacccaccag acaacccgag ggctgaggtg atatatcctc ttactgtcag ccactttgag gaactcaaag aggaacttgg agattcagga aaccggatct atttcaaaaa agcatacgtt ccgaacacaa aagggcttgc aggaactttc accagccttg cccgggaagg agagatgata agatgatacc ctatgtaaag atgatgccct atgtaaacga atacgatacc ccggagtgta aaactcttgc agagaccgca aagaaaagta tccgaacccc tgagtccctc ggactggacc gctgtatcca gtgcggagcc tgcactgctt cctgtcctgc agcccggttt acggactaca gcccccgaca gatcgtaaaa aaagtgctcg aaaatgatcg cagtgtgctt gaatccgaaa tgatctggtc ctgcttctac tgctattcct gcaatttgcg ctgtcccagg aacaacagcc ccgtaacaat cgtgcaggtt ctccggcaga tggctatcaa cgaaggaatc agggttgaaa agcttgccta tttccttgag atcggagagc acctcggaga aaacggagcc agcaaggttc cgggcgctgg catcaaaaac atggaaaaag accttggaga acgctggatt ggaattaaaa ggaagctgga accaatacgt tccgaacttg ggctcagtgc cagggatgtc aggaacaccc atggagaggt tcaggctatt cttgagagca cgggctattt cgaaagggaa agtggatca aagcaagggc ccaggaaaag ggaatccggg gttttctgaa gacggaccgc acagggacat cctgcactga aaagaagaaa aacagcggag acttaggctt tgaaagcgat agagagtata
```

-continued

```
ccggacagga agctcttact gtttaagagc tgcatggtcg ggcaggaata ccccggaatc gaaacagcca ccagttacgt gtttgaccgg cttggggtag attactgcat aaacgacgag cagtcctgct gtacaggaat aggccactat accgatgtct ttgaagggct cacaacagcc gccattgcag cccggaactt tgccgtcgcc agaaagtgcg ggtacccgaa cattacctgc ctctgttcaa cctgttatgc cataaacaag gacgcatgcg aactccttaa caccaacgat ggggtccggg aaaaagtcaa ctccatcttc cgggaaaaag gctttgatga ccttgtctat gaaaaggact ccatgaaccc cagaaccaat atctatcacg cagtcgaggt cctcctgagc aaagtcgaaa agatccggga agagataaag ttcgatttcc ccggcgttaa agcagcctct catcacgcct gccactatta taaagtcaaa taccttgacg taatcggaaa ccccgaaaac ccccagctta tagacacgat agccgaagcc tgcggggcat cccctgtgcg ctggtacgaa gatcgaaccc tcacctgcgg aatgggcttt tcccagctcc acctcaataa aagcacctct ctccaggtta ccaaaacaaa acttgacagc ctccagagag ccggtgtgga gctaatgatc catgtgtgcc cgaactgcca tatccagtac gaccgctacc agcccgttat cgaaaaagag ttcggggttg agtacgacat ggtgcacatg aacattgccc agttcgtagc cctctcaatg ggagcagacc cctacaaagt atgcggtttc cagactcact ccgtgcctct ggaaggattt cttgaaaaga ccggaataat ataatgtcca gtttcaaagt agaactggct accttttta ttacatcggg agtgaagagg g
```

Mac hdrB (mutated)

(SEQ ID NO: 6)

```
LKAIESIPDR KLLLFKSCMV GQEYPGIETA TSYVFDRLGV DYCINDEQSC CTGIGHYTDV

FEGLTTAAIA ARNFAVARKC GYPNITCLCS TCYAINKDAC ELLNTNDGVR EKVNSIFREK

GFDDLVYEKD SMNPRTNIYH AVEVLLSKVE KIREEIKFDF PGVKAASHHA CHYYKVKYLD

VIGNPENPQL IDTIAEACGA SPVRWYEDRT LTCGMGFSQL HLNKSTSLQV TKTKLDSLQR

AGVELMIHVC PNCHIQYDRY QPVIEKEFGV EYDMVHMNIA QFVALSMGAD PYKVCGFQTH

SVPLEGFLEK TGII*
```

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

---

What is claimed is:

1. A mutant heterodisulfide reductase-like protein subunit B (HdrB) polypeptide, wherein the mutant HdrB polypeptide comprises an amino acid sequence with at least 95% sequence identity to the amino acid sequence of SEQ ID NO: 3, wherein methionine at the amino acid corresponding to position 249 of SEQ ID NO: 3 is substituted with valine in the mutant HdrB polypeptide, and wherein when the mutant HdrB polypeptide is combined with a heterodisulfide reductase-like protein subunit A (HdrA) polypeptide and a heterodisulfide reductase-like protein subunit C (HdrC) polypeptide forms an HdrABC enzyme that has heterodisulfide reductase activity.

2. The mutant HdrB polypeptide of claim 1, wherein the mutant HdrB polypeptide comprises the amino acid sequence of SEQ ID NO:6.

3. A nucleic acid molecule comprising a polynucleotide encoding the mutant HdrB polypeptide of claim 1.

4. The nucleic acid molecule of claim 3, wherein the polynucleotide comprises the nucleotide sequence of SEQ ID NO: 5.

5. The nucleic acid molecule of claim 3, wherein the mutant HdrB polypeptide comprises the amino acid sequence of SEQ ID NO: 6.

6. The nucleic acid molecule of claim 1, further comprising a polynucleotide encoding a heterodisulfide reductase-like protein subunit A (HdrA) polypeptide and a polynucleotide encoding a heterodisulfide reductase-like protein subunit C (HdrC) polypeptide.

7. A microorganism comprising the nucleic acid molecule of claim 3.

8. The microorganism of claim 7, wherein the microorganism is a methanogen.

9. The microorganism of claim 8, wherein the microorganism is *Methanosarcina acetivorans*.

10. The microorganism of claim 7, wherein the nucleic acid molecule is expressed in the microorganism via an expression vector.

11. A microorganism comprising the nucleic acid molecule of claim 6.

12. The microorganism of claim 11, wherein the microorganism is a methanogen.

13. The microorganism of claim 12, wherein the microorganism is *Methanosarcina acetivorans*.

14. The microorganism of claim 11, wherein the nucleic acid molecule is expressed in the microorganism via an expression vector.

15. A method of producing methane, comprising culturing the microorganism of claim 11 under appropriate conditions to express the HdrA polypeptide, the mutant HdrB polypeptide, and the HdrC polypeptide and produce methane.

* * * * *